(12) United States Patent
Sharratt et al.

(10) Patent No.: US 7,753,844 B2
(45) Date of Patent: Jul. 13, 2010

(54) ARTICULATED RETRACTOR BLADE HOLDER

(75) Inventors: Todd W. Sharratt, Stillwater, MN (US); Todd M. Bjork, River Falls, WI (US); Robert J. Ballantine, Hudson, WI (US)

(73) Assignee: Minnesota Scientific, Inc., St. Paul, MN (US)

( * ) Notice: Subject to any disclaimer, the term of this patent is extended or adjusted under 35 U.S.C. 154(b) by 886 days.

(21) Appl. No.: 10/966,831

(22) Filed: Oct. 15, 2004

(65) Prior Publication Data

US 2005/0113645 A1 May 26, 2005

Related U.S. Application Data

(60) Provisional application No. 60/512,320, filed on Oct. 17, 2003, provisional application No. 60/535,915, filed on Jan. 12, 2004.

(51) Int. Cl.
*A61B 1/32* (2006.01)
(52) U.S. Cl. .................. 600/227; 600/201; 600/228; 600/229; 600/231
(58) Field of Classification Search ......... 606/227–231, 606/234
See application file for complete search history.

(56) References Cited

U.S. PATENT DOCUMENTS

| 1,400,616 | A | 12/1921 | McCrory et al. |
|---|---|---|---|
| 3,196,965 | A | 7/1965 | Rose |
| 3,810,462 | A | 5/1974 | Szpur |
| 4,010,741 | A | 3/1977 | Gauthier |
| 4,616,635 | A | 10/1986 | Casper et al. |
| 4,867,404 | A * | 9/1989 | Harrington et al. ............ 606/46 |
| 4,949,707 | A * | 8/1990 | LeVahn et al. ............ 600/234 |
| 5,391,180 | A | 2/1995 | Tovey et al. |
| 5,846,194 | A * | 12/1998 | Wasson et al. ............ 600/228 |
| 5,876,333 | A * | 3/1999 | Bigliani et al. ............ 600/231 |
| 5,882,298 | A | 3/1999 | Sharratt |
| 5,902,233 | A | 5/1999 | Farley et al. |
| 6,042,540 | A | 3/2000 | Johnston et al. |
| 6,042,541 | A | 3/2000 | Dobrovolny et al. |
| 6,042,542 | A | 3/2000 | Koros et al. |
| 6,210,325 | B1 * | 4/2001 | Bartie et al. ............ 600/229 |
| 6,315,718 | B1 | 11/2001 | Sharratt |
| 6,368,271 | B1 | 4/2002 | Sharratt |
| 6,416,470 | B2 | 7/2002 | Paolitto et al. |
| 6,602,190 | B2 * | 8/2003 | Dobrovolny ............ 600/234 |
| 6,685,632 | B1 | 2/2004 | Hu et al. |
| 6,695,868 | B2 | 2/2004 | Looney et al. |
| 6,733,444 | B2 | 5/2004 | Phillips |
| 6,736,775 | B2 | 5/2004 | Phillips |
| 6,837,851 | B1 | 1/2005 | Valentini et al. |
| 2003/0120132 | A1 | 6/2003 | Phillips |

FOREIGN PATENT DOCUMENTS

| EP | 0 531 710 | 5/1999 |
|---|---|---|
| WO | WO 98/27869 | 7/1998 |

* cited by examiner

*Primary Examiner*—Thomas C Barrett
*Assistant Examiner*—Matthew Lawson
(74) *Attorney, Agent, or Firm*—Peter J. Ims; Westman, Champlin & Kelly, P.A.

(57) ABSTRACT

An apparatus for holding a surgical retractor comprises a support handle and a surgical retractor holding element pivotally attached to the support handle. A rod engages the retractor holder element at a position spaced from the pivotal attachment to the support handle with the rod being movable thereby pivoting the holding element to move the position of the retractor blade of the surgical retractor.

20 Claims, 7 Drawing Sheets

Fig. 7 ure # ARTICULATED RETRACTOR BLADE HOLDER

CROSS REFERENCE TO RELATED APPLICATION(S)

This application claims priority of U.S. Provisional Application Ser. No. 60/512,320 filed on Oct. 17, 2003 entitled ARTICULATED RETRACTOR BLADE HOLDER.

This application claims priority of U.S. Provisional Application Ser. No. 60/535,915 filed on Jan. 12, 2004 entitled ARTICULATED RETRACTOR BLADE HOLDER.

BACKGROUND OF THE INVENTION

The present invention relates to a surgical retractor. More particularly, the present invention relates to an articulated holder for a surgical blade.

Surgical retractors are used to retract flesh from an incision at a surgical site. Surgical retractors typically have a blade that is fixedly attached to a handle where the blade is inserted into surgical incision. Manual force is typically applied to the retractor handle to retract flesh to expose the surgical site. With the surgical site exposed, the retractor is retained in a retracting position by clamping the handle to a retractor support apparatus positioned about the surgical site with a clamp.

However, to reposition the surgical retractor laterally, transversely and, in some instances, vertically within the surgical site, the surgical clamp must first be positioned into a non-clamping position. With the clamp in the non-clamping position, the lateral, transverse and vertical position of the surgical retractor is repositioned into a new selected position.

The surgical retractor is then secured in the new selected position by positioning the clamp in the clamping position. However, having to position the surgical clamp into the non-clamping position to make even minor adjustments to the position of the surgical retractor may add unnecessary time to the surgical procedure and inconvenience to the surgical personnel.

SUMMARY OF THE INVENTION

The present invention includes an apparatus for holding a surgical retractor, the surgical retractor having a retractor blade. The apparatus comprises a support handle having a longitudinal axis and a surgical retractor-holding element pivotally attached to the support handle. A rod engages the retractor-holding element at a position spaced from the pivotal attachment to the support handle, the rod being movable thereby pivoting the holding element to move position of the tractor blade.

In another aspect of the present invention, the apparatus for holding a surgical retractor permits pivotal movement of the retractor blade and rotational movement of the retractor blade. The retractor blade may also be moved longitudinally along an axis of its handle.

Yet in a further aspect of the present invention, the apparatus for holding the surgical retractor includes a clamp that permits movement of a retractor blade in three-dimensions, that is, in a horizontal x and y direction, and a vertical direction. The clamp is constructed such that a retractor blade of a surgical retractor may be repositioned exactly in the same position that it was previously.

DETAILED DESCRIPTION

Figure 1:
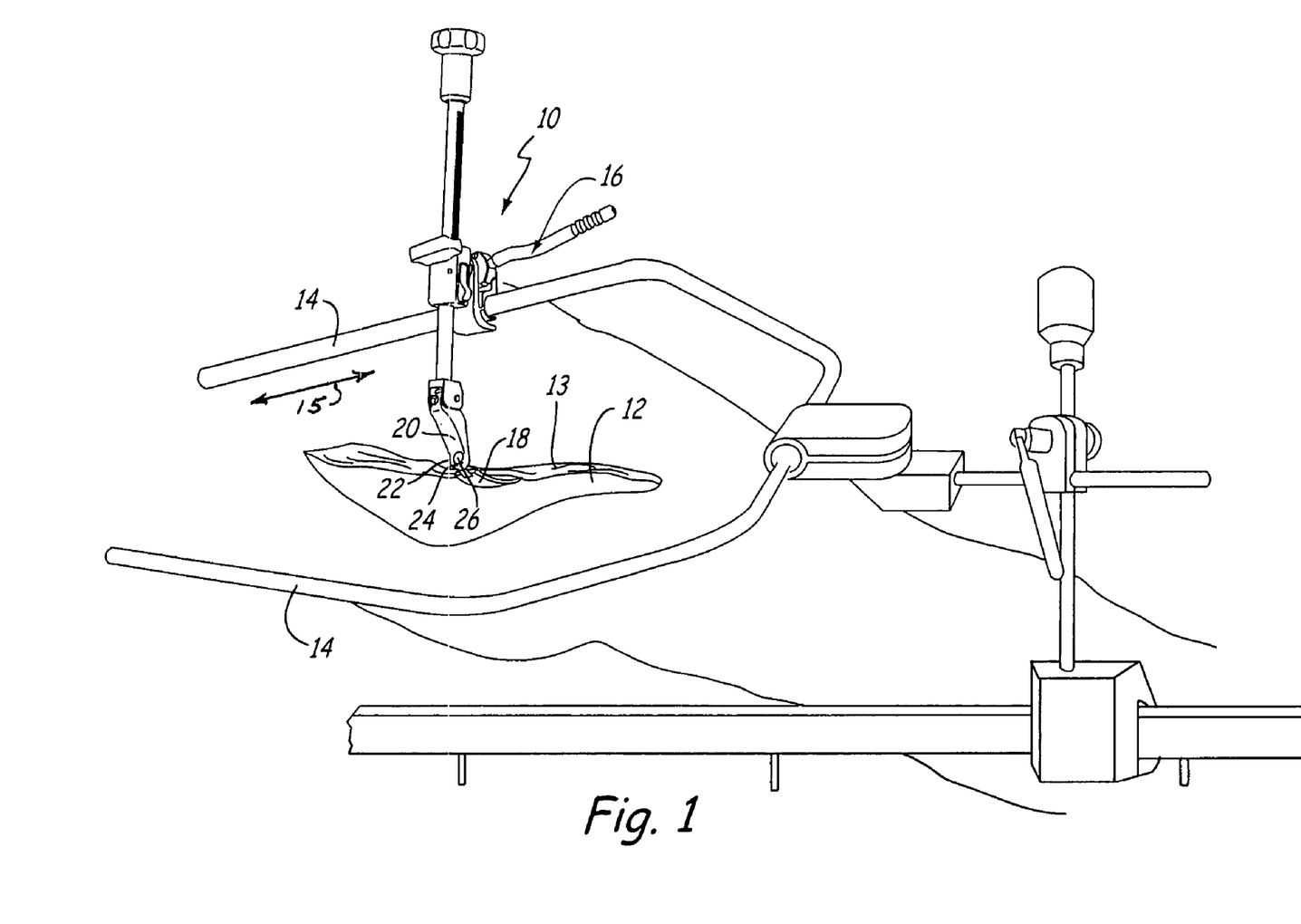
FIG. 1 is a perspective view of an articulated retractor blade holder of the present invention proximate a surgical site.

An articulated retractor blade holder of the present invention is generally illustrated at 10 in FIG. 1. The articulated retractor blade holder 10 is rotatably attached to a clamp 16 that is positioned in a selected position on a retractor support apparatus 14 that is positioned about a surgical site 12.

Figure 4:
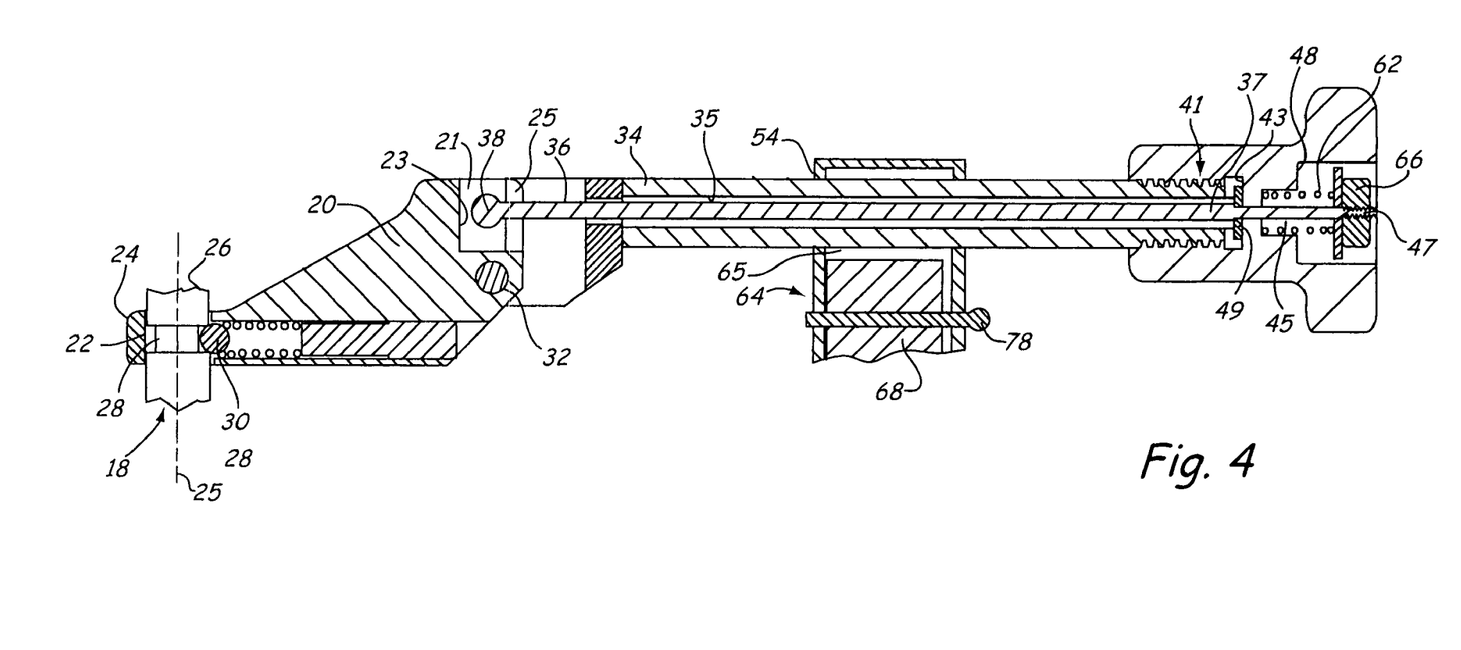
FIG. 4 is a sectional view of the articulated retractor blade holder of the present invention.

Referring to FIGS. 1 and 4, a retractor blade 18 is removably attached to a blade engaging member 20 of the articulated blade holder 10. The retractor blade 18 is attached to the blade engaging member 20 by positioning a cylindrical shaft 26 attached to the retractor blade 18 within a through bore 22 proximate a distal end 24 of the blade engaging member 20. The retractor blade 18 is rotatably retained to the blade engaging member with a spring-loaded spherical member 30 extending into the through bore 22 that engages an annular groove 28 within the cylindrical shaft 26.

The retractor blade 18 is removed from the blade engaging member 20 by applying manual force to the retractor blade 18 that overcomes the bias on the spring-loaded spherical member 30 and forces the spherical member 30 from the through bore 22. With the spring-loaded spherical member 30 forced from the through bore 22, the shaft 26 is removed from the blade engaging member 20 with manual force.

With the selected retractor blade 18 rotatably secured to the blade engaging member 20, the retractor blade 18 is positioned proximate the surgical site 12 by positioning the clamp 16 in the selected position on the retractor support apparatus 14 as illustrated in FIG. 1 the blade holder 10 be slid in the general direction of arrow 15 until clamped into position. With the clamp 16 positioned on the retractor support apparatus 14 and in the non-clamping position, the retractor blade 18 is positionable laterally, transversely and vertically within an incision 13 without having to reposition the clamp 16 on the retractor support apparatus 14.

What is meant by lateral is a direction generally along a length of the incision. What is meant by transverse is a direction generally towards or away from the incision. What is meant by vertical is a direction in which the depth of the retractor blade is adjusted within the incision.

Figure 2:
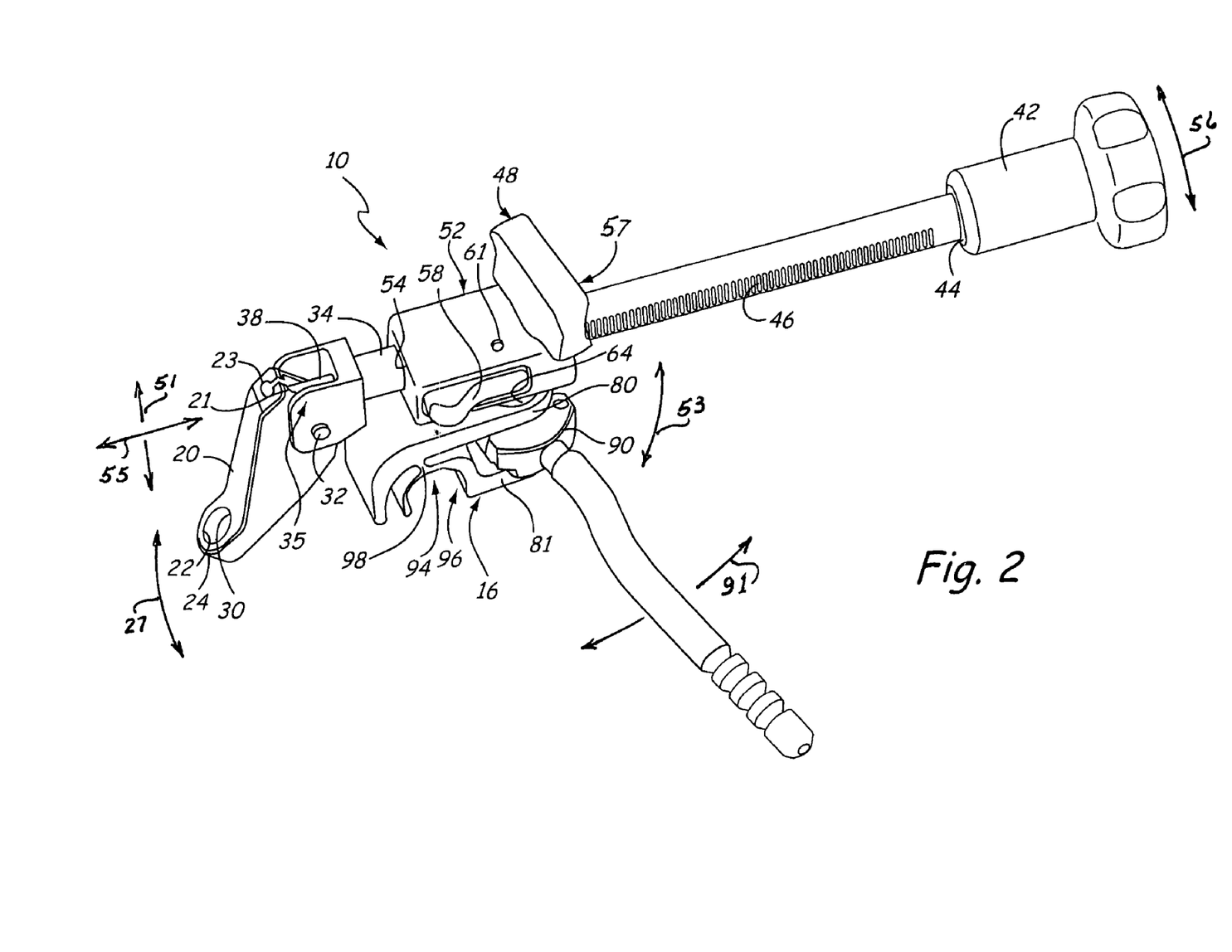
FIG. 2 is a perspective view of the articulated retractor blade holder of the present invention.
Figure 3:
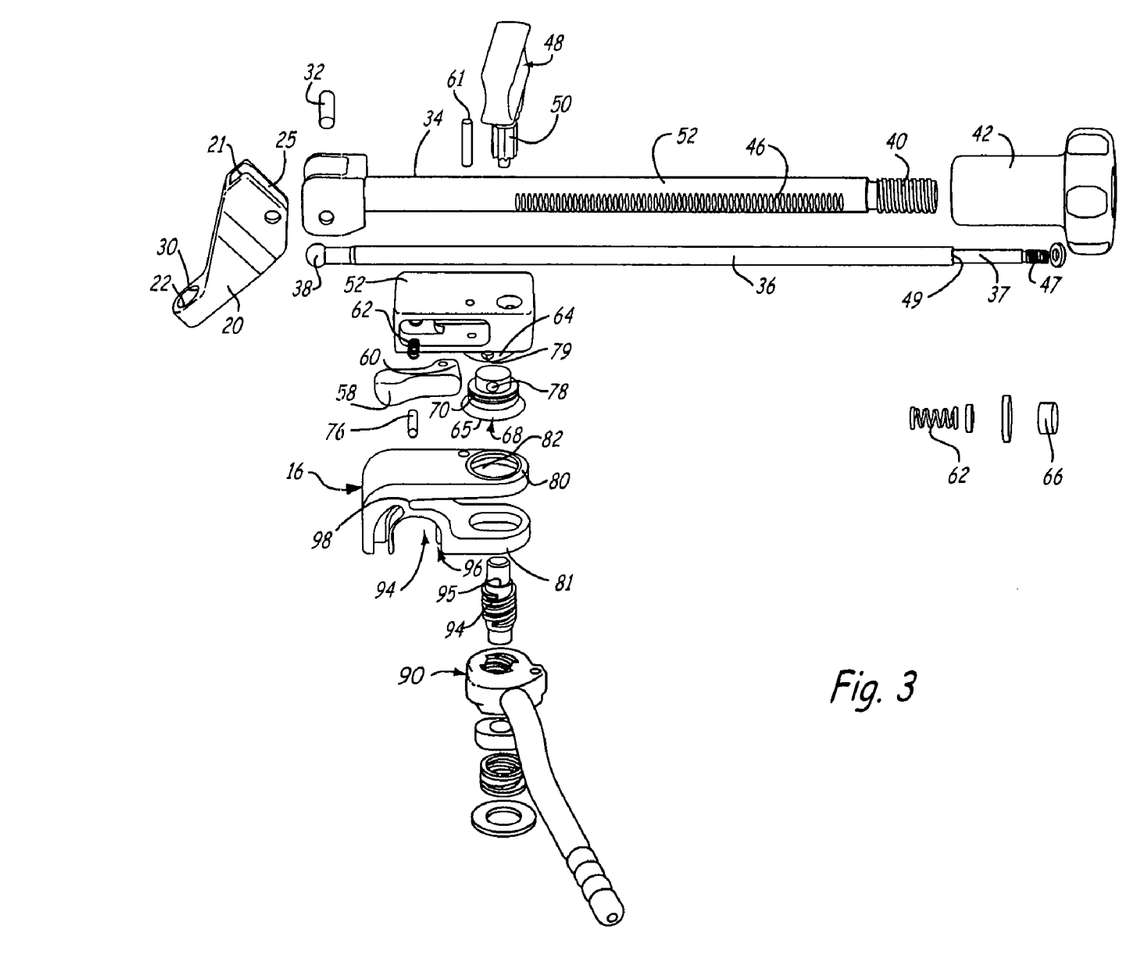
FIG. 3 is an exploded view of the articulated retractor blade holder of the present invention.

Referring to FIGS. 2-4, the retractor blade 18 is vertically positioned within the surgical site 12 by pivotally moving the blade engaging member 20 as indicated by arrow 27 about a pivot pin 32 that pivotally attaches the blade engaging member 20 to a handle 34. A push rod 36 is positioned through a cavity 35 within the handle 34, and a slot 25 extending from an outer surface and intersecting a channel 21 in the blade engaging member 20, where the slot 25 is generally aligned with the cavity 35. The push rod 36 has a proximal engaging end 38 that is positioned within the channel 21 that is also generally aligned with the cavity 35.

As the push rod 36 moves transversely with respect to the incision 13, the engaging end 38 exerts a force upon a surface 23 defining the channel 21 and causes the blade engaging member 20 to pivot about the pivot pin 32 as indicated by arrow 27. The pivotal attachment of the blade engaging member 20 to the handle 34 and the movement of the engaging end 38 within the channel 21 creates an articulated joint 33 that moves the retractor blade 18 into a selected vertical position.

The channel 21 is preferably located in a substantially orthogonal relationship to the pivotal attachment of the blade engaging member 20 to the handle 34. Other positional relationships of the channel 21 and the pivotal attachment are also within the scope of the present invention.

A distal portion 37 of the push rod 36 is non-rotatably attached to a knob 42 that threadably engages a threaded distal end 40 of the handle 34. The push rod 36 is non-rotatably secured to the knob 42 with a frictional engagement of a shoulder 49 engaging an inner surface 43 of a plate 41 that constricts a through bore in the knob 42. The push rod 36 is frictionally secured to the knob 42 by compressing a compression spring 62 positioned about the push rod 36 into an outer surface 45 of the plate 41 which forces the shoulder 49 into the inner surface 43 of the plate 41. A threaded nut 66 threadably engages a threaded end 47 of the push rod 36 to force the compression spring 62 to compress and create the frictional engagement that non-rotatably secures to the push rod 36 to the knob 42.

As the knob 42 is rotated as indicated by arrow 56, the threaded engagement of the knob 42 with the handle 34 causes the knob 42 to transversely move. As the knob 42 rotates and transversely moves, the push rod 36 also rotates and transversely moves such that the engaging end 38 applies a force to the blade engaging member 20. The force causes the engaging end 38 to move and rotate within the channel 21 and the blade engaging member 20 to pivot about the pivot pin 32.

The engaging end 38 preferably has a generally spherical configuration that engages the arcuate cylindrical surface 23 defining the channel 21. The spherical engaging member 38 is captivated within the channel 21 because a width of the slot 25 is less than a diameter of the spherical engaging end 38. However, other configurations of the engaging end 38 and the channel 21 are within the scope of the present invention provided the engaging end 38 moves within the channel 21 and is aligned with the cavity 35.

To raise the retractor blade 18, the knob 42 is rotated to threadably move the knob 42 transversely away from the blade engaging member 20. As the knob 42 moves away from the blade engaging member 20, the engaging end 38 contacts the surface 23 defining the channel 21 proximate the slot 25 and exerts a force upon the blade engaging member 20. The force urges the blade engaging member 20 to pivot upward about the pivot pin 32 and thereby raise the retractor blade 18.

To lower the retractor blade 18, the knob 42 is rotated to threadably move the knob 42 transversely towards the blade engaging member 20. As the knob 42 moves toward the blade engaging member 20, the engaging end 38 contacts the surface 23 defining the channel 21 generally opposite the slot 25 and exerts a force upon the blade engaging member 20. The force urges the blade engaging member 20 to pivot downward about the pivot pin 32, and thereby lower the retractor blade 18.

The engagement of the rotating generally spherical engaging end 38 with the generally cylindrical surface 23 allows the push rod 36 to be rapidly moved without the risk of binding the engaging end 38 within the channel 21. The engagement of the spherical surface of the engaging end 38 with the generally arcuate cylindrical surfaces 23 defining the channel 21 is non-binding whether the retractor blade 18 is in a raised or lowered position. Therefore, the articulated joint 35 of the present invention provides for a faster, non-binding vertical adjustment of the retractor blade within the surgical site than other articulated joints.

The retractor blade 18 is transversely moved as indicated by arrow 55 within the surgical site 12 with a rack and pinion mechanism 57. Other mechanisms for transversely moving the retractor blade 18 are also within the scope of the present invention.

The rack and pinion mechanism 57 includes a rack 46 on the handle 34 that is positioned within a through bore 54 of a gearbox 52. A gear 48 is positioned within a gearbox 52 such that pinions 50 of the gear 48 engage the rack 46 on the handle 34.

As the gear 48 rotates, the pinions 50 engage the rack 46 causing the handle 34 to transversely move with respect to the gear box 52. As the handle 34 moves transversely, the retractor blade 18 is also transversely moved within the surgical site 12 and into a selected transverse position.

The retractor blade 18 is retained in the selected transverse position with a pawl 58 having an engaging end 60 that is biased into engagement with the rack 46 with a compression spring 62. The pawl 58 is pivotally attached to the gearbox 52 with a pin 61. With the engaging end 60 of the pawl 58 engaging the rack 46, the handle 34 is retained in the selected transverse position and is prevented from accidentally sliding toward the surgical site 12 due a force applied to the retractor blade 18 by the retracted flesh.

The retractor blade 18 is laterally positioned as indicated by arrow 51 within the surgical site 12 by rotating the retractor blade holder 10 about a base 64 of the gearbox 52 that is rotatably captivated to an upper leg 80 of the clamp 16. As the retractor blade holder 10 in the general direction of arrow 53 is rotated about the base 64, the retractor blade 18 moves in an arcuate path thereby adjusting both the lateral and transverse position of the retractor blade 18 within the surgical site 12.

The base 64 is captivated to the upper leg 80 of the clamp 16 by positioning a cylindrical peg 68 through a through bore 82 of the upper leg 80 and positioning the cylindrical peg 66 within a recess 65 in the base 64. With the cylindrical peg 66 positioned within the recess 65 in the base 64, a pin 76 is inserted through aligned bores 78, 79 in the peg 66 and the base 64, respectively, to fixedly attach the peg 66 to the base 64 and captivate the base 64 to the upper leg 80.

In operation, the clamp 16 is placed in a non-clamping position by rotating an actuating mechanism 90 into a first non-clamping position. With the actuating mechanism 90 in the general direction of arrow 91 in the first non-clamping position, the clamp 16 can accept the retractor support arm 14 and the retractor blade holder 10 is rotatable with respect to the clamp 16.

The clamp 16 is positioned in a selected position on the retractor support arm 14 by positioning a clamping socket 94 about the retractor support arm 14. A restricted entrance 96 to the clamping socket 94 retains the clamp 16 on the retractor support arm 14 while the clamp 16 is slidably positionable on the retractor support arm 14.

With the clamp 16 positioned in a selected position on the retractor support arm 14, the retractor blade holder 10 is rotatably positioned within the surgical site 12 with manual force. Rotating the retractor blade holder 10 adjusts both the lateral position and also the transverse position of the retractor blade 18 within the surgical site 12. With the retractor blade 18 in the selected lateral position within the surgical site, the actuating mechanism 90 is rotated about a shaft 94 and into a second clamping position.

Referring to FIGS. 2 and 3, with the actuating mechanism 90 in the second position, the actuating mechanism 90 transfers a force to the lower leg 81 and also forces a shoulder 95 of the shaft 94 into the peg 66 which frictionally secures the peg 66 to the upper leg 80 of the clamp 16. The frictional engagement secures the peg 66 and the articulated retractor blade holder 10 in a selected lateral position with respect to the clamp 16.

Further, with the actuating mechanism 90 in the second position, the upper and lower legs 80, 81 are forced apart which causes a fulcrum portion 98 to flex. As the fulcrum portion 98 flexes, the clamping socket 94 constricts such that the clamp 16 frictionally engages the retractor support arm 14 and is retained in the selected position.

With the clamp 16 secured in the selected position on the retractor support arm 14 and the lateral position of the retractor blade 18 fixed within the surgical site 12, the transverse position of the retractor blade is adjusted by manipulating the gear 48 which engages the pinions 50 with the rack 46 on the handle 34. The rack and pinion mechanism 57 allows the retractor blade 18 to be moved in a transverse direction away from the surgical site 12 while the engaging end 60 of the pawl 58 engages the rack 46 to prevent movement in the opposite direction. To move the retractor blade 18 transversely towards the surgical site 12, manual force is applied to the pawl 58 to overcome the bias of the compression spring 62 to displace the engaging end 60 from the rack 46. With the engaging end 60 displaced from the rack 46, the gear 48 is rotated in an opposite direction such that the pinions 50 engage the rack 46 to move the retractor blade 18 toward the surgical site 12.

The vertical position of the retractor blade 18 is adjusted within the surgical site 12 by rotating the knob 42 attached to the push rod 36. The knob 42 threadably engages the threaded end 44 of the handle 34 and transversely moves the push rod 36, non-rotatably attached to the knob 42, with respect to the handle 34. As the push rod 36 is moved, the engaging end 38 of the push rod 36, which is positioned within the channel 21 of the blade engaging member 20, applies a force to the blade engaging member 20. As the force is applied to the blade engaging member 20, the blade engaging member 20 pivots about the pivot pin 32 and adjusts the vertical position of the retractor blade 18 within the surgical site 12.

The articulated retractor blade holder 10 in cooperation with the clamp 16 also provides a low profile device for conducting the surgical procedure. What is meant by low profile is that the articulated retractor blade holder 10 is positioned proximate the retractor support apparatus 14. By positioning the articulated retractor blade holder 10 proximate the retractor support apparatus 14, access to the surgical site 12 remains relatively open and free from obstruction.

Another advantage of the clamp 16 cooperating with the articulated retractor blade holder 10 is that the articulated retractor blade holder 10 is positionable away from a surgical site 12 while the retractor blade 18 is in a selected position within the surgical site 12. With the retractor blade 18 in the selected lateral position, the articulated retractor blade holder 10 pivots about the retractor blade 18 by moving the clamp 16 along the retractor support apparatus 14. As the clamp 16 moves along the retractor support apparatus 14, the peg 66 and the base 64 rotate with respect to the clamp 16. As the peg 66 and the base 64 rotate and the articulated retractor blade holder 10 rotates about the shaft 26, the articulated retractor blade holder 10 is moved away from the surgical site 12. With the holder 10 in a selected position, the actuating mechanism 90 is positioned into the clamping position which frictionally secures the peg 66 and the base 64 to the clamp 16 and also frictionally secures the clamp 16 to the retractor support apparatus 14.

Figure 5:
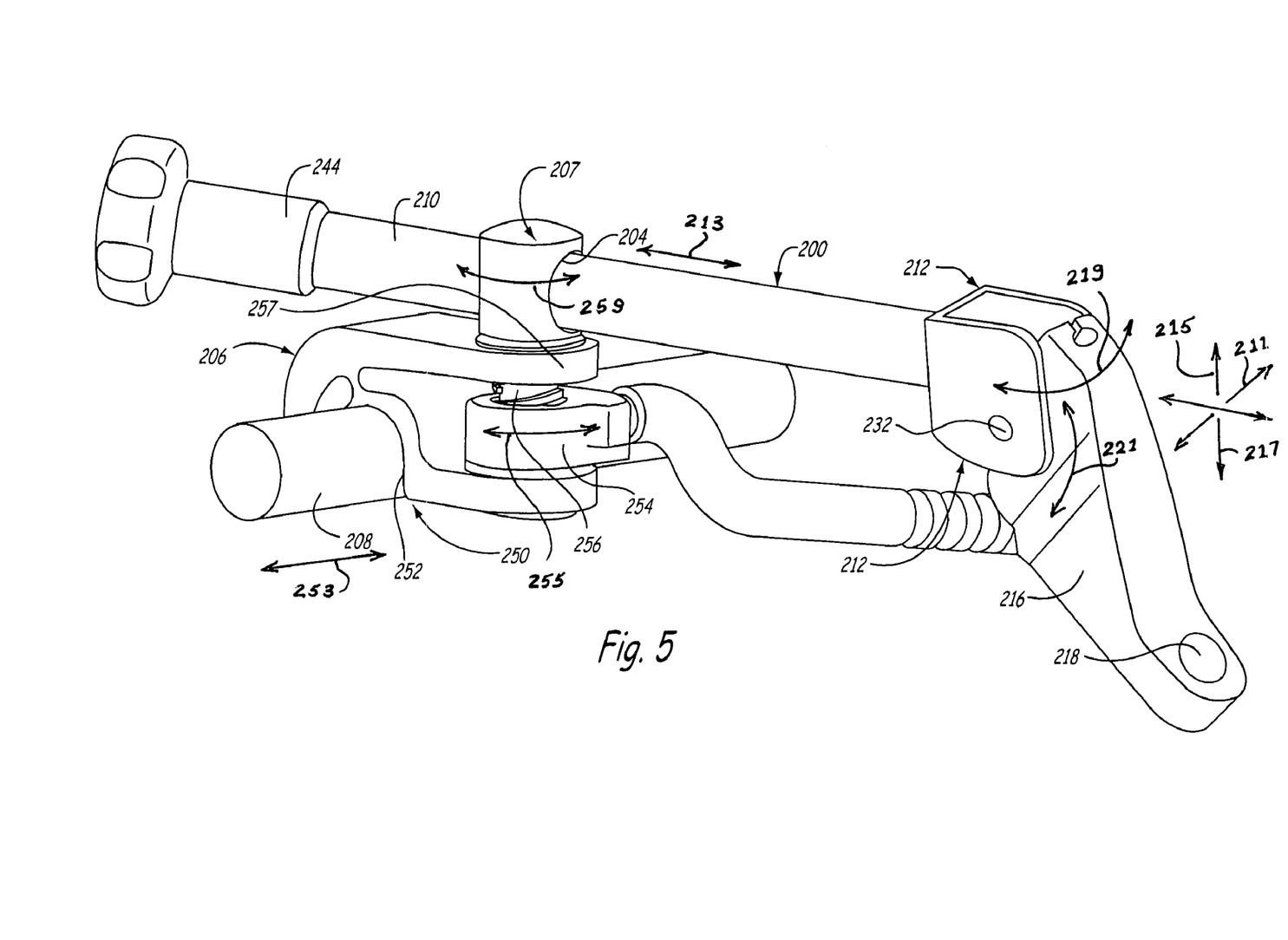
FIG. 5 is a perspective view of an alternative embodiment of an articulated retractor blade holder of the present invention retained within a clamp.
Figure 6:
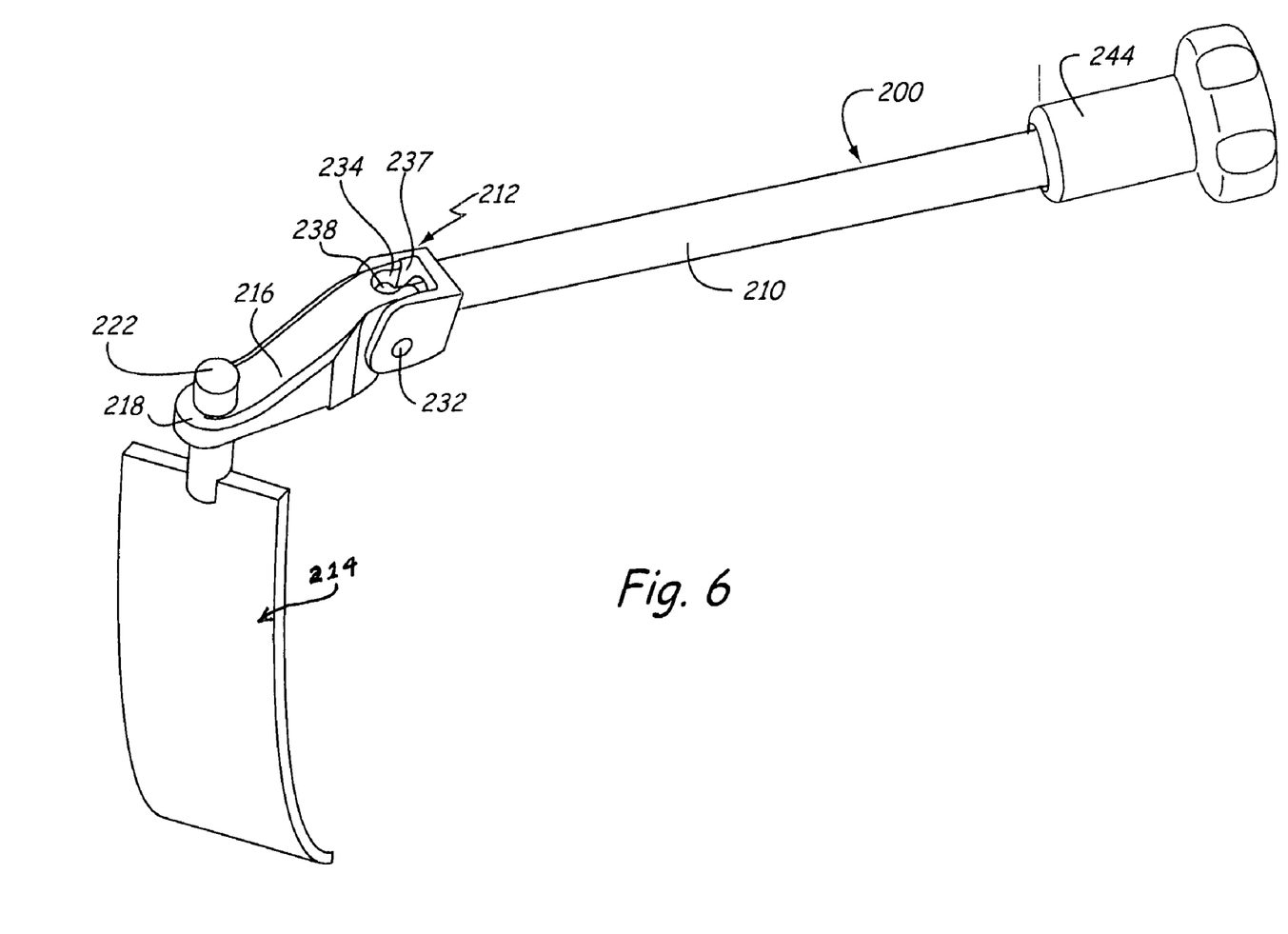
FIG. 6 is a perspective view of the alternative embodiment of an articulated retractor blade holder of the present invention.
Figure 7:
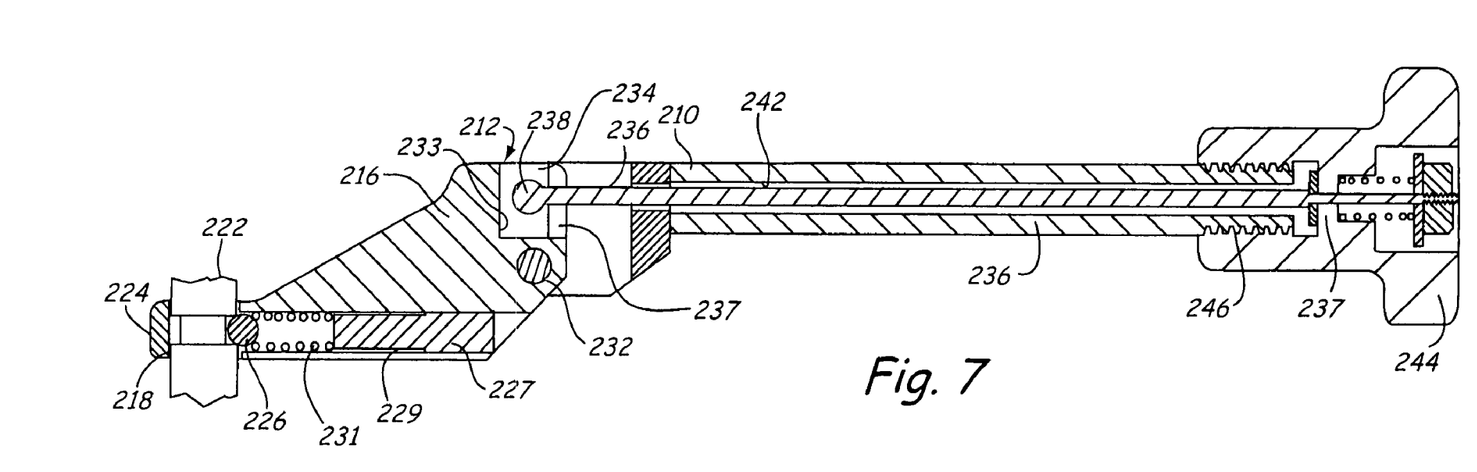
FIG. 7 is a sectional view of an articulated retractor blade holder of the present invention.

An alternative embodiment of an articulated retractor blade holder of the present invention is generally illustrated at 200 in FIGS. 5-7. The articulated retractor blade holder 200 includes an articulated joint 212 that is similar to the articulated joint 35 of the retractor blade holder 10. Unlike the retractor blade holder 10, the articulated retractor blade holder 200 is not fixedly attached to a clamp 206 and does not include a mechanical mechanism for adjusting a transverse position of the retractor blade within the surgical site.

A handle 210 of the retractor blade holder 200 is positioned within an upper clamping socket 204 of an upper clamping member 207 of the clamp 206. With the clamp 206 in the non-clamping position, the upper clamping member 207 rotates as indicated by arrow 205 within a through bore in an upper leg 257 of a lower clamping member 250 to laterally position as indicated by arrow 211 a retractor blade 214 within the surgical site (not shown). Although a rotatable upper clamping member 207 is preferred, a non-rotatable upper clamping member 207 is also within the scope of the present invention.

The handle 210 preferably has a circular cross-section and is slidably positionable within the clamping socket 204 as indicate by arrow 213. Handles having other cross-sections are also within the scope of the present invention provided the handle 210 is slidably positionable within the upper clamping socket 204 and is securable in a selected position when the clamp 206 is positioned into the clamping position. Manual force is placed upon the handle 210 to adjust a transverse position as indicated by arrow 215 of the retractor blade 214 within the surgical site.

The lower clamping member 250 is similar to the clamp 16 and has a lower clamping socket 252 similar to the clamping socket 94 for engaging the retractor support apparatus 208. When the clamp 206 is in the non-clamping position, the clamping socket 252 can accept the retractor support apparatus 208 and the lower clamping member 250 is slidably positionable on the retractor support apparatus 208 as indicated by arrow 253.

With the lower clamping member 250 in a selected position on the retractor support apparatus 208 and the retractor blade 214 in the selected lateral and transverse positions within the surgical site (note shown), an actuating mechanism 254 is rotated as indicated by arrow 255 into a clamping position where the socket 252 is constricted to frictionally secure the lower clamping member 250 to the retractor support apparatus 208. A shaft 256 threadably engaged with the actuating mechanism 254 is forced into the upper clamping socket 204 to frictionally secure the handle 210 within the upper socket 204. Otherwise the clamp socket may be rotatable in the general direction of arrow 259 thereby pivoting the blade engaging member in the general direction of arrow 219. The upper clamping member 207 is frictionally secured to the upper leg 257 of the lower clamping member 250 to prevent rotational movement of the upper clamping member 207 with respect to the lower clamping member 250.

After securing the retractor blade 214 in a selected lateral and transverse positions in the surgical site, a vertical position as indicated by arrow 217 of a retractor blade is adjusted by pivotally moving the blade engaging member 216 as generally indicated by arrow 221 about a pivot pin 232 that pivotally attaches the blade engaging member 216 to the handle 210. A push rod 236 is positioned within a cavity 242 within the handle 210, and a slot 237 within the blade engaging member 216 that is aligned with the cavity 242. The slot 237 intersects a channel 234 that accepts a proximal engaging end 238 of the push rod 236. As the push rod 236 moves within the handle 210, the engaging end 238 exerts a force upon a surface 233 defining the channel 234 and causing the blade engaging member 216 to pivot about the pivot pin 32.

As the blade engaging member 216 pivots about the pivot pin 232, the retractor blade 214 is manipulated into a selected vertical position. The channel 234 is preferably located in a substantially orthogonal relationship to the pivotal attachment of the blade engaging member 216 to the handle 210, although other positional relationships of the channel 234 and the pivotal attachment are within the scope of the present invention.

A distal portion 237 of the push rod 236 is non-rotatably attached to a knob 24 as previously described in the embodiment 10. The knob 244 threadably engages a threaded distal end 246 of the handle 210. As the knob 244 is rotated, the threaded engagement of the knob 244 with the handle 210 causes the knob 244 to transversely move. As the knob 244 rotates and transversely moves, the push rod 236 also rotates and transversely moves such that the engaging end 238 applies a force to the blade engaging member 216. The force causes the engaging end 238 to move within the channel 234 and the blade engaging member 216 to pivot about the pivot pin 232. The movement of the engaging end 238 within the channel 234 along with the pivotal attachment of the blade engaging member 216 to the handle 210 creates the articulated joint 212 that moves the retractor blade 18.

The engaging end 238 preferably has a generally spherical configuration that engages the surface 233 generally arcuate cylinder defining the channel 234 in the blade engaging member 216. The engaging end 238 is captivated within the channel 234 because a width of the slot 237 is less than a diameter of the spherical engaging end 238.

To raise the retractor blade 214, the knob is rotated to threadably move the knob 242 transversely away from the blade engaging member 216. As the knob 242 moves away from the blade engaging member 216, the engaging end 238 contact the surface 233 defining the channel 234 proximate the slot 237 and exerts a force upon the blade engaging member 216. The force urges the blade engaging member 216 to pivot upward about the pivot pin 232 and thereby raise the retractor blade 214.

To lower the retractor blade 214, the knob 244 is rotated to threadably move the knob 244 transversely towards the blade engaging member 216. As the knob 244 moves toward the blade engaging member 216, the engaging end 238 contacts the surface 233 defining the channel 234 generally opposite the slot 237 and exerts a force upon the blade engaging member 216. The force urges the blade engaging member 216 to pivot downward about the pivot pin 232, and thereby lower the retractor blade 216.

The retractor blade 214 is removably attached to the blade engaging member 216 by positioning a cylindrical shaft 222 attached to the retractor blade 214 within a through bore 218 proximate a distal end of the blade engaging member 216. The retractor blade 214 is rotatably retained to the blade engaging member 216 with a spring-loaded spherical member 226 extending into the through bore 218 that engages an annular groove 224 within the cylindrical shaft 222.

Although the present invention has been described with reference to preferred embodiments, workers skilled in the art will recognize that changes may be made in form and detail without departing from the spirit and scope of the invention.

What is claimed is:

1. An apparatus for holding a surgical retractor, the surgical retractor having a retractor blade, the apparatus comprising:
a support handle having a longitudinal axis;
a surgical retractor-holding element pivotally attached to the support handle;
a rod engaging the retractor holding element at a position spaced from the pivotal attachment to the support handle, the rod being movable thereby pivoting the holding element to move the position of the retractor blade; and
a clamp attached to the support handle wherein the clamp attaches to a retractor support.

2. The apparatus of claim 1 and further comprising a base slidably attached to the support handle and rotatably attached to the clamp such that angular movement of the retractor blade occurs with respect to the clamp.

3. The apparatus of claim 1 and wherein the clamp further comprises a clamping socket for attaching the apparatus to the retractor support and wherein the clamp permits movement along the retractor support when the clamp is in a non-clamping position.

4. The apparatus of claim 1 where the support handle has external threads and further including a knob threadably engaging the threads for movement along the handle and wherein the knob engages the rod and moves the rod when the knob is turned about the external threads of the handle.

5. The apparatus of claim 1, further comprising a second clamping member, the second clamping member permitting movement of the support handle along its longitudinal axis and rotational movement of the support handle when the first clamping member is in a non-clamping position.

6. The apparatus of claim 1 and further comprising a gear rack longitudinally disposed on the support handle and a clamp having one clamping element for clamping onto a retractor support and another clamping element for engaging the support handle the other clamping element including a pinion gear for engaging the gear rack such that the support handle moves along its longitudinal axis when the pinion gear is turned.

7. The apparatus of claim 6 wherein the another clamping member is rotatable thereby permitting rotation of the support handle when the another clamping member is in a non-clamping position.

8. The apparatus of claim 6 and further including a pawl for engaging the gear rack and being pivotally secured within the other clamping member thereby inhibiting movement of the support handle in one direction.

9. An articulate joint comprising:
a handle having a cavity therethrough;
an engaging member comprising a channel having a substantially circular cross-sectional perimeter and a slot intersecting the channel and extending to an outer surface and being generally aligned with the longitudinal cavity and wherein the engaging member pivotally attaches to an end of the handle; and
a rod positioned through the cavity and the slot comprising substantially spherical engaging end positioned within the channel and wherein the rod moves within the handle to provide a force to the engaging member and causes the engaging member to pivot into a selected position.

10. The articulated joint of claim 9 and further comprising a knob non-rotatably attached to the rod and wherein the knob operably engages the handle to move the rod within the cavity and move the engaging end within the channel to pivotally move the engaging member.

11. The articulated joint of claim 9 and further comprising:
a rack positioned on the handle; and
a gear having a plurality of pinions wherein the plurality of pinions engage the rack and wherein the plurality of pinions engage the rack as the gear rotates to transversely move the engaging member.

12. The articulated joint of claim 9 and further comprising:
a base operably attached to the handle; and
a clamping member rotatably attached to the base and wherein the clamping member is positionable between a non-clamping position wherein the base rotates and a clamping position where the base is fixed to the clamping member.

13. An assembly attachable to a retractor support apparatus positioned about a surgical site and for moving a retractor blade in three-dimensions within a surgical site, the assembly comprising:
an engaging member and wherein the retractor blade attaches to the engaging member;
a handle having mechanical mechanism operably attached thereto;
an articulated joint attaching the engaging member and the handle;
a base attached to the handle and rotatably secured to a clamp wherein the clamp is attached to the retractor support apparatus and wherein the rotation of the base moves the retractor blade longitudinally within the surgical and manipulation of the mechanical mechanism moves the retractor blade transversely within the surgical site and wherein the articulated joint is manipulated to move the retractor blade vertically within the surgical site.

14. The assembly of claim 13 and wherein the base is rotatably attached to the clamping member and wherein the clamping member is manipulated to fix a rotational position of the base.

15. The assembly of claim 13 and wherein the mechanical mechanism comprises:
a rack on the handle; and
a gear comprising a plurality of pinions and wherein the plurality of pinions engages the rack to transversely move the handle as the gear rotates.

16. The assembly of claim 13, wherein the articulated joint comprises:
a pivotal attachment of the engaging member to the handle and wherein the engaging member comprises a channel; and
a push rod slidably positioned within the handle and having an engaging end and wherein the engaging end is positioned within the channel and moves to apply to force to the engaging member such that the engaging member pivots with respect to the handle.

17. The assembly of claim 16 and further comprising a knob non-rotatably attached to the push rod and wherein the knob operably engages the handle to move the engaging end within the channel to pivotally move the engaging member.

18. An articulated retractor holder comprising:
a handle having a longitudinal cavity;
an engaging member for retaining a retractor blade comprising a channel having a substantially circular cross-sectional perimeter and a slot extending to an outer surface and intersecting a channel and wherein the slot generally aligns with the longitudinal cavity and wherein the engaging member pivotally attaches to an end of the handle; and
a rod positioned through the longitudinal cavity and comprising a substantially spherical engaging end positioned within the channel and wherein the rod moves within the handle to provide a force to the engaging member and causes the engaging member to pivot into a selected position.

19. The articulated retractor blade holder of claim 18 and further comprising:
a rack positioned on the handle; and
a gear having a plurality of pinions wherein the plurality of pinions engage the rack and wherein the plurality of pinions engage the rack as the gear rotates to transversely move the engaging member.

20. The articulated retractor blade holder of claim 18 and further comprising:
a base operably attached to the handle; and
a clamping member rotatably attached to the base and wherein the clamping member is positionable between a non-clamping position wherein the base rotates and a clamping position where the base is fixed to the clamping member.

* * * * *